(12) United States Patent
Milbocker et al.

(10) Patent No.: US 9,095,734 B2
(45) Date of Patent: Aug. 4, 2015

(54) NITRIC OXIDE RELEASING MULTIFUNCTIONAL POLYMERS

(71) Applicant: Maple Ridge Group, LLC, New York, NY (US)

(72) Inventors: Michael Milbocker, Holliston, MA (US); Kenneth Rothaus, New York, NY (US)

(73) Assignee: Maple Ridge Group, LLC, New York, NY (US)

( * ) Notice: Subject to any disclaimer, the term of this patent is extended or adjusted under 35 U.S.C. 154(b) by 292 days.

(21) Appl. No.: 13/802,208

(22) Filed: Mar. 13, 2013

(65) Prior Publication Data

US 2014/0271523 A1  Sep. 18, 2014

(51) Int. Cl.

| A61K 31/74 | (2006.01) |
|---|---|
| A61Q 19/10 | (2006.01) |
| A61K 31/785 | (2006.01) |
| A61L 27/34 | (2006.01) |
| A61L 27/54 | (2006.01) |
| A61K 8/90 | (2006.01) |

(52) U.S. Cl.
CPC . *A61Q 19/10* (2013.01); *A61K 8/90* (2013.01); *A61K 31/785* (2013.01); *A61L 27/34* (2013.01); *A61L 27/54* (2013.01); *A61L 2300/114* (2013.01)

(58) Field of Classification Search
CPC .................................................. A61K 31/785
See application file for complete search history.

(56) References Cited

U.S. PATENT DOCUMENTS

2010/0255062 A1* 10/2010 Kalivretenos et al. ........ 424/440

FOREIGN PATENT DOCUMENTS

WO   WO 2009064861 A2 *  5/2009

\* cited by examiner

*Primary Examiner* — Paul Dickinson
(74) *Attorney, Agent, or Firm* — W. David Wallace; Holland & Knight LLP

(57) ABSTRACT

A molecule for stabilizing a bioactive chemical group capable of releasing nitric oxide in vivo is described. The molecule possesses multi-functionality, enabling the delivery of multiple nitric oxide precursors on a single molecule. In some embodiments, a tissue or prosthetic bonding group is attached to one of the functional arms of the molecule making the molecule of the present invention localizing to tissue or an implant.

20 Claims, 4 Drawing Sheets

NITRIC OXIDE RELEASING MULTIFUNCTIONAL POLYMERS

This application claims the benefit of the priority of U.S. provisional application 61/610,049, which is hereby incorporated by reference in its entirety.

BACKGROUND

Nitric oxide (NO) is a messenger molecule that plays an important physiological role, both intracellular and intercellular, in anti-platelet aggregation and anti-platelet activation, vascular relaxation, neurotransmission, and immune response. It has been proposed that synthetic materials that release low levels of NO or possess NO precursors on their surface would therefore more closely simulate the natural activity of endothelial cells, and therefore would improve tissue healing and the formation of vascularized tissue in proximity to an implant.

Nitric oxide (NO), a simple diatomic molecule, is a powerful signaling compound that plays a diverse and complex role in cellular physiology. NO is associated with endothelial cells, neural cells and macrophages. Mammalian cells synthesize NO using a two-step enzymatic process that oxidizes L-arginine to N-.omega.-hydroxy-L-arginine, which is then converted into L-citrulline and an uncharged NO free radical. Three different nitric oxide synthase enzymes regulate NO production. Neuronal nitric oxide synthase (NOSI, or nNOS) is formed within neuronal tissue and plays an essential role in neurotransmission. Endothelial nitric oxide synthase (NOS3 or eNOS), is secreted by endothelial cells and induces vasodilatation. Inducible nitric oxide synthase (NOS2 or iNOS) is principally found in macrophages, hepatocytes and chondrocytes and is associated with immune cytotoxicity.

NOS and eNOS are enzymes that regulate the release of small amounts of NO. NO activates guanylate cyclase which elevates cyclic guanosine monophosphate (cGMP) concentrations which in turn increase intracellular Ca+2 levels. Increased intracellular Ca+2 concentrations result in smooth muscle relaxation which accounts for NO's vasodilating effects.

Biological disorders associated with the implantation of a medical device, for example excessive fibrotic encapsulation, can be prophylactically ameliorated by supplying the repair site with therapeutic levels of NO. This can be accomplished by stimulating the endogenous production of NO or using exogenous NO sources.

Regarding stimulation of endogenous NO formation, nitric oxide synthases (NOS) produce NO by replacing a N=C double bond with an O=C double bond. Researchers have focused on activation of enzymatic pathways with excess NO metabolic precursors like L-arginine and L-lysine. Therefore, there is interest in a metabolic precursor which may not itself release NO but may catalyze endogenous NO release. Synthetic precursors that release NO are of interest in this connection.

The exogenous administration of gaseous nitric oxide is generally not feasible due to the highly toxic, short-lived, and relatively insoluble nature of NO in physiological fluids. As a result, the clinical use of gaseous NO is largely restricted to the treatment of neonates with conditions such as persistent pulmonary hypertension. Alternatively, however, the systemic delivery of exogenous NO with such precursor drugs as nitroglycerin has long enjoyed widespread use in the medical management of angina pectoris associated with atherosclerotic narrowing of coronary arteries. There are problems with the use of agents such as nitroglycerin. Nitroglycerin requires a variety of enzymes and cofactors in order to release NO, repeated use of this agent over short intervals produces a diminishing therapeutic benefit. By contrast, if too much nitroglycerin is initially given to the patient, it can have devastating side effects including severe hypotension and free radical cell damage.

One potential method for overcoming the disadvantages associated with NO precursor drug administration is to provide NO-releasing molecules that do not require activation by endogenous enzyme systems.

NO and precursors of NO are typically unstable, and are too reactive to be used without some means of stabilizing the molecule until it reaches the treatment site. NO can be delivered to treatment sites in an individual by means of polymers and small molecules which release NO. However, these polymers and small molecules typically release NO rapidly. As a result, they have short shelf lives and rapidly lose their ability to deliver NO under physiological conditions. For example, the lifetime of S-nitroso-D,L-penicillamine and S-nitroso-cysteine in physiological solution is no more than about an hour. As a result of the rapid rate of NO release by these compositions, it is difficult to deliver sufficient quantities of NO to a treatment site for extended periods of time or to control the amount of NO delivered. Additionally, rapid release of NO and consequently high concentrations of NO is not always beneficial, especially in a healing promotion modality where low concentrations are required throughout the healing period, which can last up to six months.

Nitric oxide and nitric oxide donor compounds have been used for treating cardiovascular diseases, hypertension, inflammation, pain, fever, gastrointestinal disorders, ophthalmic diseases, glaucoma, ocular hypertension, hepatic disorders, renal diseases, nephropathies, diabetes, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation, vascular diseases, neurodegenerative disorders, metabolic syndrome, Reynolds' syndrome, scleroderma, muscular dystrophies such as Duchenne and Becker dystrophies.

These treatment successes would be enhanced by providing a compound that supports endogenous NO formation or NO release that is slow and of long duration. Accordingly, the therapeutic compound must be stabilized against rapid degradation and elimination from the body. This requires the NO precursor be stabilized on the delivery molecule and the delivery molecule itself be of sufficient size or bonded to an implant to mitigate its early elimination from the body.

A very important class of NO precursor agents is the nitric oxide-nucleophile complexes. Methods for treating cardiovascular disorders in a mammal with certain nitric oxide-nucleophile complexes have been disclosed. These compounds contain an anionic $N_2O_2^-$-group or derivatives in a diazeniumdiolate. Many of these compounds have proven especially promising pharmacologically because, unlike nitrovasodilators such as nitroprusside and nitroglycerin, they release nitric oxide without first having to be activated. The only other series of drugs currently known to be capable of releasing nitric oxide purely spontaneously is the S-nitrosothiol series, compounds of structure R—S—NO. There are manufacturing complications associated with the synthesis of R—S—NO complexes. Nevertheless, these structures tend to degrade rapidly in vivo and are unstable to ambient conditions in storage.

While N-based diazeniumdiolate polymers have the advantages of localized spontaneous release of NO under physiological conditions, a major disadvantage associated with all N-based diazeniumdiolates is their potential to form carcinogenic nitrosamines upon decomposition. Some nitrosamines are extremely carcinogenic and the potential for nitrosamine formation limits the N-based diazeniumdiolate class of NO donors from consideration as therapeutic agents based on safety issues.

Therefore, if these structures are to be used, there is a need to make the byproducts of these structures more biocompatible. For example, there is a need to both stabilize the NO-releasing moiety in vivo, and to render the resulting molecule more biocompatible.

Currently, NO generation is determined by water uptake (such as in the case of diazeniumdiolates) or the intensity of light (as with iron nitrosyls). However, blood already contains a host of species that are derived from, or are physiologically-generated in vivo that may be reduced to NO. These species include nitrites, nitrates, and a host of nitrosothiols (e.g. nitrosoglutathione, nitroso albumin, etc.). The presence of these species raises the possibility of recycling these species back to nitric oxide in the presence of a synthetic molecule. Thus, there is a need for a synthetic molecule that acts synergistically with in vivo constituents that reduce to NO.

Alternatively, to treat a disorder with nitric oxide over a period of time, two compounds could be co-administered-one compound with a quick release of NO and a second compound with an NO release rate several times longer than the first compound. Unfortunately, at present, a suitable long term NO release moiety is not commercially available.

As another alternative, the same compound could be administered multiple times in order to provide a lasting treatment. However, this method increases the cost of treatment because of increased dosing and subjects the patient to increased exposure to any potential side effects.

The most promising NO precursors are those with a cyclic polyamine structure. For example, adducts of cyclic polyamine piperazine with nitric oxide have been studied. The bisdiazeniumdiolate of piperazine has been reported to have a biphasic release of NO with an initial half-life of 2.3 minutes and a secondary half-life of 5.0 minutes. In fact due to the similarity in the initial and secondary release rates for the bisdiazeniumdiolate of piperazine, it was initially believed that the two release rates were identical. Because the profile of the biphasic release of NO from the bisdiazeniumdiolate of piperazine was on such a similar time scale, and because the second half-life of NO release was only 5.0 minutes, such a compound is not practical for use in implant situations where tissue healing around the implant is desired. In addition, the use of piperazine diazeniumdiolate in pharmaceutical compositions is not desirable because of the potential toxicity of its possible nitrosopiperazine metabolite.

NO has also been found effective against infection. NO may contribute to the morbidity of infection by acting as a vasodilator, myocardial depressant, and cytotoxic mediator. On the other hand, microvascular, cytoprotective, immuno-regulatory, and antimicrobial properties of NO have a salutary and probably essential role in the infected host. However, in the context of NO-releasing synthetic molecules, there is potential for direct elimination of a pathogen. Yet, to date direct elimination of a pathogen by NO release has not been demonstrated.

In the context of antimicrobial activity, most antimicrobials are cytotoxic, and at a minimum interfere with or reduce healing in the content of prosthetic implantation. Thus, there is a need for a bioactive agent that both enhances the healing response and directly eliminates microbes. The potential of NO to up-regulate vascularization in healing, supply more blood flow to a repair site, and diminish the incidence of exogenous and endogenous microbial colonization of a repair site or prosthetic is of clinical interest.

In recognizing the aforementioned aspects of the current state of the art, the following patents and applications are relevant in the present context.

U.S. Pat. Nos. 5,155,137 and 5,250,550 describe complexes of nitric oxide and polyamines which are useful in treating cardiovascular disorders, including hypertension. The disclosed compounds release nitric oxide (endothelium-derived relaxing factor) under physiological conditions in a sustained and controllable fashion, and possess long mechanisms of action.

U.S. Pat. Nos. 5,366,997 and 5,405,919 describe oxygen substituted derivatives of nucleophile-nitric oxide adducts as nitric oxide donor prodrugs.

U.S. Pat. Nos. 5,525,357 and 5,650,447 describe a polymeric composition capable of releasing nitric oxide including a polymer and a nitric oxide-releasing $N_2O_2$-functional group bound to the polymer; pharmaceutical compositions including the polymeric composition.

U.S. Pat. Nos. 7,087,709 and 7,417,109 describe novel polymers derivatized with at least one —$NO_x$ group per 1200 atomic mass unit of the polymer. X is one or two. In one embodiment, the polymer is an S-nitrosylated polymer and is prepared by reacting a polythiolated polymer with a nitrosylating agent under conditions suitable for nitrosylating free thiol groups.

U.S. Pat. No. 7,226,586 describes extremely hydrophobic nitric oxide (NO) releasing polymers. The extremely hydrophobic NO-releasing polymers provided are extensively cross-linked polyamine-derivatized divinylbenzene diazeniumdiolates.

U.S. Pat. No. 7,425,218 describes an implant or intravascular stent comprising a polymeric composition capable of releasing nitric oxide under physiological conditions.

U.S. Pat. No. 7,569,559 describes compositions comprising carbon-based diazeniumdiolates that release nitric oxide (NO). The carbon-based diazeniumdiolated molecules release NO spontaneously under physiological conditions without subsequent nitrosamine formation.

U.S. Pat. No. 7,763,283 describes biocompatible materials that have the ability to release nitric oxide (NO) in situ at the surface-blood interface when in contact with blood. The materials which may be polymers (e.g., polyurethane, poly(vinyl chloride), silicone rubbers), metals, such as stainless steel, carbon, and the like are provided with biocatalysts or biomimetic catalysts on their surface that have nitrite, nitrate, and/or nitrosothiol-reducing capability.

U.S. Pat. No. 7,811,600 describes implantable medical devices comprising nitric oxide (NO) donating polymers comprising polymer backbones having at least one cyclic amine disposed thereon.

U.S. Pat. No. 7,829,553 describes compositions comprising carbon-based diazeniumdiolates attached to hydrophobic polymers that releases nitric oxide (NO).

U.S. Pat. No. 7,928,079 describes compounds capable of releasing nitric oxide wherein the compounds comprise a saccharide and at least one nitric oxide-releasing diazeniumdiolate [$N_2O_2$] functional group, which is bonded directly to a carbon atom of the saccharide, and methods for preparing the same.

U.S. Pat. No. 7,928,096 describes polydiazeniumdiolated cyclic polyamines with polyphasic nitric oxide release and related compounds, compositions comprising same and methods of using same.

U.S. Pat. No. 7,968,664 describes novel nitric oxide-releasing polymers that comprise at least two adjacent units derived from acrylonitrile monomer units and containing at least one carbon-bound diazeniumdiolate.

U.S. Pat. No. 8,003,811 describes nitric oxide donors and pharmaceutically acceptable salts or stereoisomers.

U.S. Pat. No. 8,021,679 describes implantable medical devices and/or coatings comprise NO-releasing biodegradable polymers derived from [1,4]oxazepan-7-one and its derivatives.

U.S. Pat. No. 8,034,384 describes a material including a surface and a reactive agent that is located at the surface of the material, covalently attached to a backbone of the material, and/or located within the material. The reactive agent has nitrite reductase activity, nitrate reductase activity, and/or nitrosothiol reductase activity.

U.S. App. No. 20100303891 describes a bio-adhesive supra-macromolecular complex containing an NO releasing group.

U.S. App. No. 20110117164 describes a method for increasing, prolonging, and/or controlling the release rates of nitric oxide (NO) from polymeric materials containing NO adducts.

Despite the promise of the nitric oxide/nucleophile adducts that have been investigated, their implantable applications are limited by their tendency to disassociate from the implant or repair site and distribute systemically. Distribution systemically tends to compromise the local benefit of being implanted along with an implant or at a surgical repair site. Thus there remains a need for nitric oxide-releasing compositions which are capable of concentrating the effect of the nitric oxide release to a situs of application and for which nitric oxide release may be controlled for effective dosing.

SUMMARY OF THE INVENTION

Thus, despite the extensive literature available on NO and nitric oxide-releasing compounds, there remains a need for stable nitric oxide-releasing polymers that exhibit a sustained release of nitric oxide that can be readily prepared, even from commercially available polymers.

Moreover, there exists a need for a medical device, such as a stent, vascular graft, or orthopedic prosthetic, comprised of or coated with a material capable of continuously releasing NO from the first instance of blood contact to days or weeks following implantation.

It is, therefore, a principal object of the present invention to provide a polymeric composition comprising a biopolymer backbone to which is bound a NO-releasing functional group and which is capable of releasing NO under physiological conditions.

It is another object of the present invention to provide a polymeric composition comprising a biopolymer backbone to which is bound a NO-releasing functional group whose release of NO is such that a prolonged biological effect can be attained.

Another object of the present invention is to provide pharmaceutical compositions comprising such biopolymeric compositions.

Another object of the present invention is to provide cosmetic and topical compositions comprising such biopolymeric compositions. Another object of the present invention is to provide implant modifying compositions comprising such biopolymeric compositions. Another object of the present invention is to provide implantable compositions comprising such biopolymeric compositions. Another object of the present invention is to provide a method of treating a biological disorder involving the administration of such biopolymeric compositions topically.

These and other objects and advantages of the present invention, as well as additional inventive features, will be apparent from the description of the invention provided herein.

DETAILED DESCRIPTION OF THE INVENTION

Figure 1:
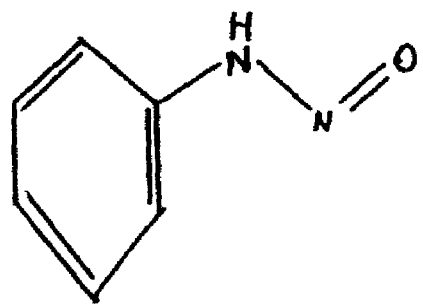
FIG. 1 shows an isocyanate attached to an aromatic ring, forming a nitrosamine group. In the figure, the isocyanate group is —NH—N=O, but more general isocyanates, for example RN(—R)—N=O, can be used in the system of the invention.

This invention relates generally to the generation of nitric oxide in situ, and more particularly to biocompatible materials having surfaces that are capable of generation of nitric oxide in situ. This invention relates to biocompatible materials capable of delivering nitric oxide in situ and also possessing a tissue bonding or prosthetic bonding functionality.

The present invention also relates to medical devices having coatings of the present molecule, wherein the coatings include biocompatible polymers based on an aryl group attached to an aromatic ring. More specifically, the present invention relates to medical devices having coatings, which include nitric oxide-releasing groups, an implant bonding functionality, and a polymeric backbone of hydrophilic and hydrophobic segments.

More specifically, the present invention relates to aromatic ring-based N-diazeniumdiolate nitric oxide-releasing polymers. The present invention also provides methods for a novel class of coatings in which NO-releasing moiety is stabilized by an aromatic ring, where this structure may be covalently linked to a surface, whereby the release of NO imparts increased biocompatibility, antimicrobial functionality or other beneficial properties to the coated surface. A preferred application for this class of coatings would be in medical devices.

Chemical compounds of the present invention comprise aromatic ring stabilized NO-releasing moiety R2. R2 can be nitrosamine N(—R3)-N=O or nonoate N—N(O)NO moieties attached to a polymeric backbone R1, to form a delivery molecule containing the form R1-N(—R3)-N=O or R1-N—N(O)NO. The polymeric backbone R1 is preferably multifunctional (multi-armed) and capable of concentrating multiple nitrosamine and nonoate moieties singly or in combination, on a single delivery molecule. Additionally, one or more of the polymeric backbone arms may be substituted with a tissue bonding or prosthetic bonding moiety.

In addition to its functional aspects, the polymeric backbone R1 provides shielding benefits to the NO precursor groups. R1 is comprised of hydrophilic groups and hydrophobic groups. The hydrophilic groups are positioned such that the overall delivery molecule is biocompatible and does not precipitate a foreign body response which may degrade or otherwise render less functional the precursor NO moieties. The hydrophobic groups are positioned such that water is repelled from the aromatic ring structure comprising the NO precursor groups. Clearly, the degree of hydrophobic shielding can be adjusted by the position, size and distribution of hydrophobic and hydrophilic segments on the polymer backbone.

The intervening aromatic ring structure, positioned between the polymeric backbone R1 and the NO precursor R2, balances the nitrosamine or nonoate group with an opposing urethane or urea group connecting the polymeric backbone to the aromatic ring. Due to the resonant structure of aromatic rings, the effect of the opposing urethane or urea group tends to increase positive charge in the vicinity of the NO precursor functional group, and consequently tends to increase the half-life of nitric oxide generation.

The mechanism of this rate retardation may be attributable simply to repulsive electrostatic interactions, which inhibit attack of positively charged H ions on the NO precursor functional group and slows the rate of its H-catalyzed decomposition.

The invention described herein provides novel nitric oxide-releasing ether-urethane/urea-aromatic ring-based polymers ("EUA polymers"). The polymers of the invention preferably comprise at least two adjacent NO precursor units derived from nitrosamine or nonoate segments and contain at least one aromatic ring associated with each NO precursor segment.

In addition, although less preferred, the present invention can embody other nitric oxide-releasing moieties in the NO precursor position, including cyclic amidine compounds based on nitrile-containing compounds. Other nitric oxide releasing moieties that may be beneficially stabilized by the present EUA structure include diazeniumdiolated cyanoalkanes and diazeniumdiolated (poly)acrylonitrile.

These EUA-based polymers can be used to enhance the resistance to microbial colonization and promote healing of tissue associated with an implanted medical devices. Alternatively, these EUA-molecules can be used in a cosmetic, antibiotic or pharmaceutical mode.

Some embodiments of the present invention are implantable medical devices and coatings for medical devices made from one or more of the NO-releasing polymers of the present invention. These NO-releasing medical devices and coating made in accordance with the teachings of the present invention include embodiments wherein one or more additional bioactive agent is attached to one of the arms of the polymeric backbone. The bioactive agent can be released in vivo or function as an interface between the NO-releasing polymer and a device or tissue. Preferably, said interface is a covalent bond.

Suitable bioactive agents include, but are not limited to, FKBP 12 binding compounds such as zotarolimus, estrogens, chaperone inhibitors, protease inhibitors, protein-tyrosine kinase inhibitors, leptomycin B, peroxisome proliferator-activated receptor gamma ligands (PPAR.gamma.), hypothemycin, bisphosphonates, epidermal growth factor inhibitors, antibodies, proteasome inhibitors, antibiotics, anti-inflammatories, anti-sense nucleotides and transforming nucleic acids.

Alternatively, the EUA-based polymers of the present invention may be delivered as individual molecules with all their functional arms occupied with NO-releasing groups where in the polymer is eluted from a substrate polymer in a predetermined fashion. Exemplary embodiments of a delivery device scenarios include, but are not limited to, drug-eluting vascular stents, soft tissue repair devices, bone prosthetics, and tissue anti-adhesion surgical barrier devices.

The reaction of isocyanate functionality with gaseous nitric oxide is:

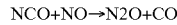

Referring to FIG. 1, when the isocyanate is attached to an aromatic ring, such as is the case of the aromatic diisocyanates, the reaction forms a nitrosamine RN(—R)—N═O group.

Figure 2:
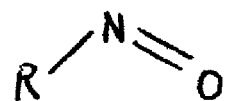
FIG. 2 shows a simple structure R—N=O, having a terminal nitrosyl group. R could be a benzene ring as in FIG. 1, but more complex structures, such as RN—(NO)—N=O, are also suitable.

The nitrosamine group is unstable and degrades into NO in the presence of water. Another possible structure is nonoate of form RN—(NO⁻)—N═O, which is characterized by a terminal nitrosyl group as depicted in FIG. 2.

Figure 3:
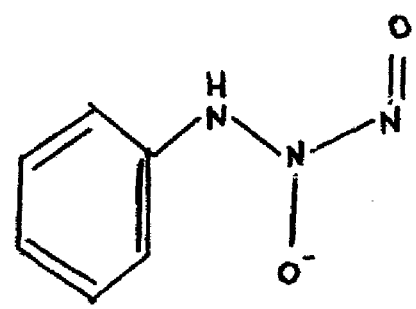
FIG. 3 shows a structure having three sequential nitrogen atoms in a structure.

Referring to FIG. 3, these compounds are unusual in having three sequential nitrogen atoms: an amine functional group, a bridging NO⁻ group, and a terminal nitrosyl group. This structure can be synthesized using the above nitrosamine structure doubly reacted with another NO molecule in acidic conditions to form the structure depicted in FIG. 3. This structure is again unstable in water and liberates NO in an aqueous environment.

When the diisocyanate is reacted with an alcohol, such as polyethylene glycol, polypropylene glycol or combinations of these ethers, in sufficient quantities that free NCO groups are pendant, then the diisocyanate forms a urethane or urea link (if the glycol is aminated) between the glycol and the aromatic ring of the diisocyanate. The free NCO group can then participate in nitrosamination or nonoate formation when exposed to gaseous NO. The alcohol in this structure is a nucleophile, and bends towards electronegativity of the oxygen, which is substantially greater than that of carbon and hydrogen. Consequently, the covalent bonds of this functional group are polarized so that oxygen is electron rich and both carbon and hydrogen are electrophilic, and the NO-releasing group is partially shielded from environmental water.

The aromaticity of the benzene ring between NO-releasing moiety and ether moiety stabilizes the NO-releasing moiety. The aromatic ring is a conjugated ring of unsaturated bonds, lone pairs, or empty orbitals exhibit a stabilization stronger than would be expected by the stabilization of conjugation alone.

Aromaticity can also be considered a manifestation of cyclic delocalization and of resonance. This is usually considered to be because electrons are free to cycle around circular arrangements of atoms which are alternately single- and double-bonded to one another. These bonds may be seen as a hybrid of a single bond and a double bond, each bond in the ring identical to every other. The model for benzene consists of two resonance forms, which corresponds to the double and single bonds superimposing to give rise to six one-and-a-half bonds. Benzene is a more stable molecule than would be expected without accounting for charge delocalization.

One skilled in the art will also recognize the theoretical possibility that some NO can be sequestered in these polymers by electrostatic interaction with the pi electrons contained in the multiple bonds (i.e., to form clathrate-type or sandwich-like structures). Indeed, to some extent, these and other possible structures may exist in the materials of the present invention.

Figure 4:
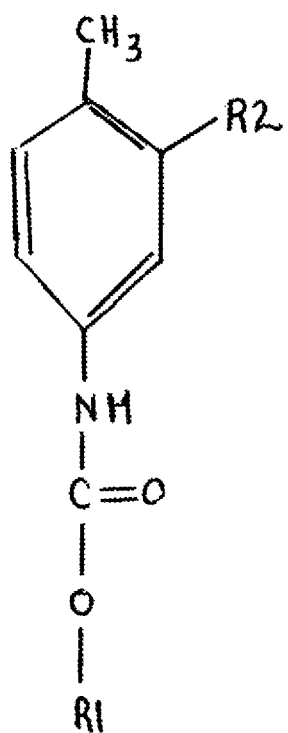
FIG. 4 illustrates the general structure of the embodiments of the present invention.

FIG. 4 illustrates the general structure of the molecules of the present invention. R1 is a biocompatible molecule, preferably containing multifunctional hydroxyl or amine groups which can be reacted with an aromatic diisocyanate to form urethane or urea links. In FIG. 4 a urethane link is illustrated linking the biocompatible multifunctional polymer to the benzene ring of an aromatic diisocyanate. R2 is a NO releasing group, typically of the nonoate or nitrosamine structure. The diisocyanate used in the example depicted in FIG. 4 is 2,4-toluene diisocyanate.

The incorporation of at multifunctional polymer at R1 increases the capacity of a molecule to deliver NO and the stability of the molecule. The combination of increased stability and capacity to deliver NO results in a high NO potency, a controlled delivery of NO and extended treatment and storage lives for the polymer. A further advantage of these polymers is that they lack the brittleness of other NO-delivering compositions and have sufficient elasticity to coat and adhere under physiological conditions to medical devices such as stents.

The R1 polymers of the present invention can be prepared from polymers having a multiplicity of nucleophilic groups. Suitable nucleophilic groups include amines, thiols, hydroxyls, hydroxylamines, hydrazines, amides, guanadines, imines, aromatic rings and nucleophilic carbon atoms.

In particular, R1 may be a triol of ethylene oxide and propylene oxide units distributed so as to render the entire NO-releasing structure biocompatible. For example, the triol may consist of a copolymer consisting of 25% propylene oxide units and 75% ethylene oxide units, or their glycols. Alternatively, diols of ethylene oxide and propylene oxide or copolymers of these can be grafted to a small trifunctional center such as trimethylolpropane through urethane links.

In some cases an absorbable polymer backbone is desired. Typical absorbable, biocompatible links are ester, polysaccharide, or caprolactone moieties. For example, a lactide can be grafted in between the ether units to provide degradation by hydrolysis.

Accordingly, the present invention provides a method of releasing nitric oxide from a nitric oxide-releasing multifunctional base polymer, preferably a polymer of the present invention releases NO over a period of at least one day (i.e., at least about 24 hours), more preferably at least three days (i.e., at least about 72 hours), more preferably at least 1 week, and most preferably at least 1 month.

Figure 5:
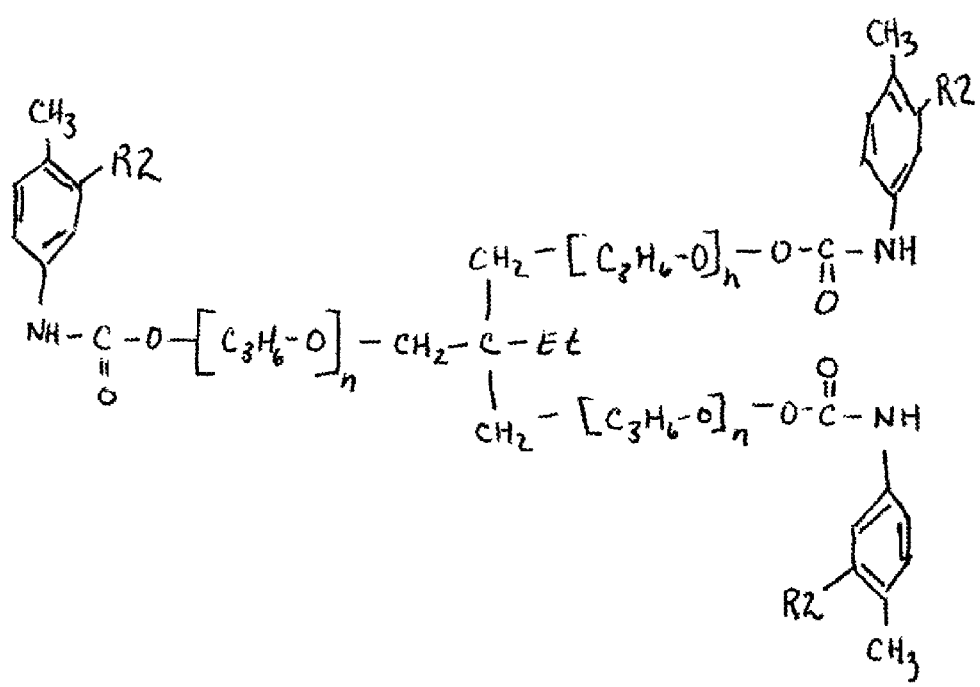
FIG. 5 shows an example of polymeric structures of the invention.

Referring to FIG. 5, preferably base polymeric structures have multifunctional centric compositions in the R1 position, as opposed to chain multifunctional structure. Such centric base molecules are called star molecules, and the simplest are trifunctional, e.g., a triol of poloxamer. A poloxamer triol in the R1 position is illustrated in FIG. 5.

The multifunctional aspect of the base polymer can serve to provide compounds that have a multiphasic release of NO. While the ring stabilized form of the NO releasing structures of the present invention have much extended release times compared to NO release structures attached to linear chains that are singly or multiply functional.

Figure 6:
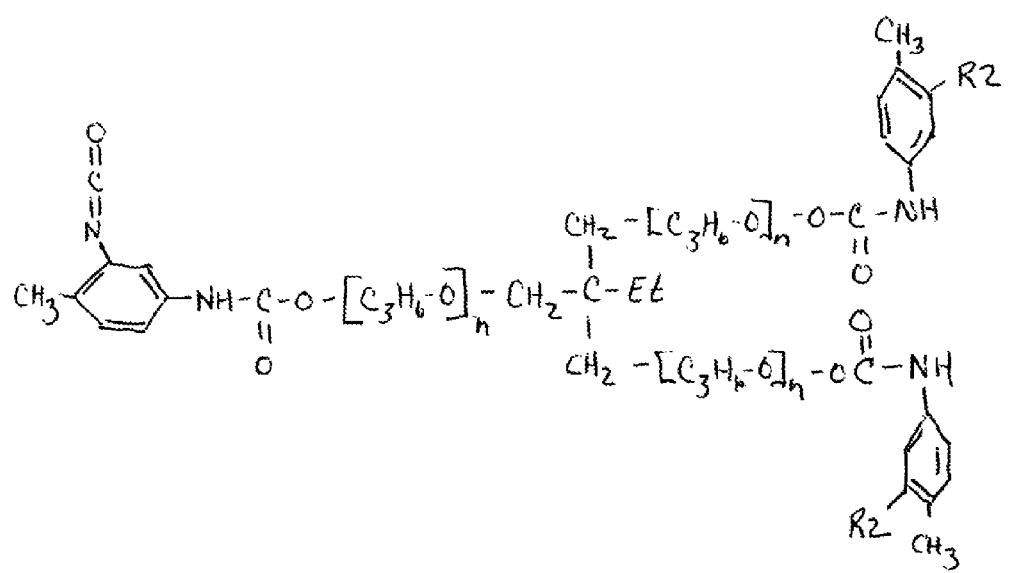
FIG. 6 shows an embodiment of the present invention which has an reactive isocyanate group on one arm.

As illustrated in FIG. 6, an additional embodiment of the present invention relates to medical devices and medical device coatings comprising polymers, wherein the polymers and co-polymers possess a functional isocyanate group on one of the base polymer arms. Such isocyanates are capable of bonding to other molecules with an amine or hydroxyl functionality. More specifically, the present invention relates to medical devices and medical device coatings having which include nitric oxide (NO) releasing, biocompatible, biodegradable polymers and co-polymers.

Thus the present invention provides at least two means for enhancing a medical device's biocompatibility and/or providing for in situ drug delivery to a treatment site. In one embodiment of the present invention the biocompatible, biodegradable, NO-releasing polymers and co-polymers made in accordance with the teachings of the present invention are used to provide coatings for implantable medical devices; the coating may or may not include an additional bioactive agent at one of the R2 positions. For example, one arm of a base polymer triol structure contains an NO-releasing group, another arm contains an isocyanate groups, and a third arm contains an additional bioactive group.

In another embodiment of the present invention the entire medical device is made using the biocompatible, biodegradable, NO-releasing polymers and co-polymers made in accordance with the teachings of the present invention.

Medical devices made in accordance with the teachings of the present invention include, but are not limited to, vascular stents, stent grafts, urethral stent, biliary stents, catheters, sutures, ocular devices, heart valves, shunts, pacemakers, bone screws and anchors, orthopedic prostheses, protective plates and other prosthetic devices, both functional and cosmetic.

Similar benefits might be expected to result from polyphasic NO release for a host of other disorders, especially those that can be treated by modulating cyclic GMP levels. Acute respiratory crises might be treated with an effective amount of a poly- or biphasic NO donor whose first phase very rapidly dilates the airways and quickly reverses the associated pulmonary hypertension and whose subsequent phase(s) provide(s) the "maintenance dose" required to sustain these beneficial effects. A similar outcome is anticipated for treating impotence. In a coated prosthetic modality, an initial release rate of NO may act anti-microbially, both in terms of up-regulating immune response and acting directly, and a secondary release rate which serves to promote healing. Healing may be promoted by causing more blood to be delivered to the treatment area, as well as promote the formation of new vessels at the healing site.

The compounds and compositions of the invention are useful for treating an animal, e.g., a mammal such as a human, for infection with, for example, a virus (e.g., hepatitis, HIV), a bacterium, or a parasite. The method comprises administering topically or internally to the animal, e.g., human, an amount of a compound of the invention or composition thereof sufficient to treat the infection in the animal.

The method of treating cancer with a compound of the present invention can be used in combination with other known treatment methods, such as radiation, surgery, or the administration of other active agents, such as adjuvants or other anti-cancer agents and their prodrugs. Examples of cyotoxic agents and their prodrugs include genistein, okadaic acid, 1-.beta.-D-arabinofuranosyl-cytosine, arabinofuranosyl-5-aza-cytosine, cisplatin, carboplatin, actinomycin D, asparaginase, bis-chloro-ethyl-nitroso-urea, bleomycin, chlorambucil, cyclohexyl-chloro-ethyl-nitroso-urea, cytosine arabinoside, daunomycin, etoposide, hydroxyurea, melphalan, mercaptopurine, mitomycin C, nitrogen mustard, procarbazine, teniposide, thioguanine, thiotepa, vincristine, 5-fluorouracil, 5-fluorocytosine, adriamycin, cyclophosphamide, methotrexate, vinblastine, doxorubicin, leucovorin, taxol, anti-estrogen agents such as tamoxifen, intracellular antibodies against oncogenes, the flavonol quercetin, guan-mu-tong extract, retinoids such as fenretinide, nontoxic retinoid analogues such as N-(4-hydroxyphenyl)-retinamide (HPR), and monoterpenes such as limonene, perillyl alcohol and sobrerol.

The method of treating cancer with a compound of the present invention can be combined with still other methods of prophylactic and therapeutic treatment. Such methods include those that target destruction of cancer cells, e.g., by targeting of cell-surface markers, receptor ligands, e.g., ligands to gastrin-releasing peptide-like receptors, tumor-associated antigens, e.g., the 57 kD cytokeratin or the antigen recognized by the monoclonal antibody GB24, the extracellular matrix glycoprotein tamascin, antisense constructs to mRNA of oncogenes such as c-fos, homeobox genes that are expressed in cancer cells but not normal cells, tumor-infiltrating lymphocytes that express cytokines, RGD-containing peptides and proteins, which are administered following surgery, lipophilic drug-containing liposomes to which are covalently conjugated monoclonal antibodies for targeting to cancer cells, low fat diet, moderate physical exercise and hormonal modulation. For prostate cancer, anti-testosterone agents can be used as well as inhibitors of cellular proliferation produced by prostatic stromal cells and C-CAM, an epithelial cell adhesion molecule.

The following examples are meant to be illustrative, and not limiting.

Example 1

Synthesis of Base Polymer

A poloxamer triol, such as dry (<300 ppm H2O) Multranol 3901 (Bayer, Morristown, N.J.) containing 1 mole of hydroxyl groups, is combined with toluene diisocyanate containing 2 moles of NCO groups in a glass reactor equipped with a stirrer, heating jacket and temperature sensor. The reactor is purged with dry nitrogen and the mixture stirred. The reaction volume is heated to 40° C. and allowed to react until the exotherm has subsided. Then the temperature of the reactor is increased in 5° C. increments, stopping after each increment to let the exotherm subside, until a temperature of 65° C. is reached. The reaction mixture is further reacted until 1 mole of isocyanate group is consumed. This end point can be determined by measuring the % NCO.

Example 2

An NO-Releasing Polymer

The polymer base of Example 1 is placed in a reactor. The reactor is purged with dry nitrogen. The volume is stirred and gaseous NO is delivered to the reaction volume. The polymer base will immediately begin to react with the introduced NO, turning a deep red. A solvent may be used in cases where the polymer base is too viscous. For example, acetone can be used, and the solvent later removed by vacuum. Alternatively an inert solvent such as propylene carbonate may be used. The reaction is continued for approximately 12 hours at room temperature, in less time at elevated temperature. The reaction is complete when all residual NCO functionality is consumed.

Example 3

A Topical Antimicrobial

The NO-releasing polymer if Example 2 is mixed in an inert base with pleasing cosmetic attributes. The principal requirement for long shelf-life is that the base mixture possess the lowest practical water content, typically less than 300 ppm H2O. For example, a mixture of butylene glycol, sodium lauroyl lactylate, propylene glycol, poloxamer 407 and laureth-4 result in a foaming composition suitable for delivering the NO-releasing polymer of Example 2 as a shower wash. Effective concentrations of NO-releasing polymer in topical compositions is generally between 0.1% and 0.3%.

Example 4

An NO-Releasing Polymer with Tissue/Prosthetic Bonding Functionality

The polymer base of Example 1 is placed in a reactor. The reactor is purged with dry nitrogen. The volume is stirred and gaseous NO is delivered to the reaction volume. The polymer base will immediately begin to react with the introduced NO, turning a deep red. A solvent may be used in cases where the polymer base is too viscous. For example, acetone can be used, and the solvent later removed by vacuum. Alternatively an inert solvent such as propylene carbonate may be used. The reaction is continued until approximately $2/3$ of the NCO functionality is consumed. Clearly, any degree of tissue bonding functionality can be obtained by controlling the amount of NCO functionality that is consumed, typically greater than $1/3$ of the NCO functionality and less than approximately $5/6$ of the NCO functionality.

Example 5

A Prosthetic Coated with an NO-Releasing Polymer

A prosthetic is coated with a solution of polymer base of Example 1. The polymer base may be diluted with a volatile solvent such as toluene or acetone. The coated prosthetic is then allowed to cure partially in a humid environment. While still in a fluid state, the coated prosthetic is then transferred to a closed box that has been purged with dry nitrogen. The box is filled gaseous NO and the coated prosthetic allowed to reacted with the NO until all isocyanate functionality is consumed.

In summary, the materials and functions of the device of the invention include the following: In one aspect of the invention, a nitric oxide releasing polymer comprises: a) a biocompatible base polymer, b) at least one aromatic ring, and c) a NO-releasing group. The biocompatible base polymer is attached to the aromatic ring through a urethane or urea link at one position on the aromatic ring, and the NO-releasing group is attached at another site on the same aromatic ring or on an additional aromatic ring. The biocompatible base polymer is multifunctional, and may be a poloxamer triol comprised of polypropylene and polyethylene segments. The NO-releasing groups may be selected from one or more of the following: a) nitrosamine, b) nonoate, or c) clathrate of NO.

The nitric oxide releasing polymer may be made by reacting a multi-functional alcohol with a diisocyanate until all hydroxyl functionality is consumed to provide a macro multi-isocyanate, and the by reacting said macro multi-isocyanate with gaseous nitric oxide until all isocyanate functionality is consumed.

The nitric oxide releasing polymer may be used as a cosmetic base. It may also comprise a nitric oxide releasing polymer with bonding functionality comprising: a) a biocompatible base polymer, b) at least one aromatic ring with pendant isocyanate functionality, and c) a NO-releasing group, wherein the biocompatible base polymer is attached to the aromatic ring through a urethane or urea link at one position on the aromatic ring and the NO-releasing group attached at another site on the same or additional aromatic ring, and an isocyanate group at one or more locations on one or more aromatic rings. The polymer may be coated with a nitric oxide releasing polymer. The polymer may form an implantable composition comprising isocyanate groups that are further reacted with a bioactive molecule.

A method of synthesizing a nitric oxide releasing polymer with bonding functionality may comprise the steps of: a) reacting a multi-functional alcohol with a diisocyanate until all hydroxyl functionality is consumed to provide a macro multi-isocyanate, and b) said macro multi-isocyanate reacted with gaseous nitric oxide until a portion of isocyanate functionality is consumed.

A method of coating a prosthetic with a nitric oxide releasing polymer may comprise the steps of: a) coating the prosthetic with the polymer; b) partially polymerizing the polymer on the prosthetic, and c) further reacting any remaining isocyanate groups with gaseous nitric oxide.

The nitric oxide releasing polymer of the invention is suitable for treatment of a patient, or for the coating of a prosthetic, for example by the reaction of a nitric oxide releasing polymer with a bioactive molecule to coat a prosthetic. It is also useful for coating a prosthetic, directly or by coating the prosthetic with a bioactive molecule, or with a nitric oxide releasing polymer, and/or with a cosmetic base.

Embodiments of the invention have been described in detail, and other embodiments and modifications will be apparent to those skilled in the art. The following claims are intended to include all such embodiments and modifications, and equivalents.

What is claimed is:

1. A nitric oxide releasing polymer comprising a biocompatible base polymer, at least one aromatic ring, and a NO-releasing group, wherein said biocompatible base polymer is attached to said aromatic ring through a urethane or urea link at one position on said aromatic ring, and said NO-releasing group is attached at another site.

2. The nitric oxide releasing polymer of claim 1, where the NO-releasing group is attached to the same aromatic ring.

3. The nitric oxide releasing polymer of claim 1, where the NO-releasing group is attached to an additional aromatic ring.

4. The nitric oxide releasing polymer of claim 1 wherein said biocompatible base polymer is multifunctional.

5. The nitric oxide releasing polymer of claim 4 wherein said biocompatible base polymer is a poloxamer triol comprised of polypropylene and polyethylene segments.

6. The nitric oxide releasing polymer of claim 1 wherein said NO-releasing groups are selected from one or more of a nitrosamine, a nonoate, and a clathrate of NO.

7. The nitric oxide releasing polymer of claim 1, further comprising a pendant isocyanate group at one or more locations on said polymer.

8. The nitric oxide releasing polymer of claim 1, further comprising bonding functionality, said bonding functionality comprising at least one aromatic ring with pendant isocyanate functionality.

9. The nitric oxide releasing polymer of claim 1, further comprising a cosmetic base.

10. The nitric oxide releasing polymer of claim 1 wherein said biocompatible base polymer is attached to the aromatic ring through a urethane or urea link at one position on the aromatic ring, and the NO-releasing group is attached at another site on the same or additional aromatic ring, and an isocyanate group is attached at one or more locations on one or more aromatic rings.

11. The nitric oxide releasing polymer of claim 1, in combination with a cosmetic base.

12. The nitric oxide releasing polymer of claim 1, wherein said polymer forms a prosthetic material.

13. The nitric oxide releasing polymer of claim 12, wherein said prosthetic material is implanted.

14. The nitric oxide releasing polymer of claim 12, wherein said prosthetic material is used as a coating.

15. The nitric oxide releasing polymer of claim 12, wherein said prosthetic material is further combined with a bioactive molecule.

16. The nitric oxide releasing polymer of claim 12, wherein said prosthetic material is multifunctional.

17. The nitric oxide releasing polymer of claim 12 wherein said prosthetic material comprises isocyanate groups, which are further reacted with a bioactive molecule.

18. The nitric oxide releasing polymer of claim 12 wherein said prosthetic material is coated with a nitric oxide releasing polymer comprising the steps of coating the prosthetic with said polymer, partially polymerizing said polymer in situ on the prosthetic, and further reacting any remaining isocyanate groups with gaseous nitric oxide.

19. A method of synthesizing a nitric oxide releasing polymer, comprising the steps of reacting a multi-functional alcohol with a diisocyanate until all hydroxyl functionality is consumed, to provide a macro multi-isocyanate; and then reacting said macro multi-isocyanate with gaseous nitric oxide until a portion of the isocyanate functionality of said macro multi-isocyanate is consumed.

20. The method of claim 19 wherein said reaction with gaseous nitric oxide is continued until all isocyanate functionality is consumed.

* * * * *